United States Patent [19]

Sharpe et al.

[11] 4,158,308
[45] Jun. 19, 1979

[54] TIME-VARIABLE BANDWIDTH ULTRASONIC TESTING APPARATUS

[75] Inventors: Donald E. Sharpe, Woodbury; Howard E. Van Valkenburg, New Fairfield, both of Conn.

[73] Assignee: Automation Industries, Inc., Los Angeles, Calif.

[21] Appl. No.: 835,506

[22] Filed: Sep. 22, 1977

[51] Int. Cl.$^2$ ............................................. G01N 29/04
[52] U.S. Cl. ........................................ 73/609; 73/629
[58] Field of Search ................. 73/602, 614, 615, 627, 73/629, 631, 609, 620–624, 632, 610, 611, 613

[56] References Cited

U.S. PATENT DOCUMENTS

| 3,309,914 | 3/1967 | Weighart | 73/615 |
| 3,367,173 | 2/1968 | Uphoff | 73/631 |
| 3,924,454 | 12/1975 | McElroy et al. | 73/628 |
| 4,016,750 | 4/1977 | Green | 73/629 |

FOREIGN PATENT DOCUMENTS 1308800 10/1962 France ............................................. 73/631

OTHER PUBLICATIONS

R. Goldman, Ultrasonic Technology, Reinhold Publ. Co., N.Y., 1962, pp. 181–185.

Primary Examiner—Stephen A. Kreitman
Attorney, Agent, or Firm—Robert Hockfield

[57] ABSTRACT

An ultrasonic nondestructive testing system of the pulse-echo type is disclosed including an echo-signal-translator exhibiting a bandwidth that is varied to achieve excellent near-surface resolution while affording deep inspection of an object under test.

4 Claims, 5 Drawing Figures

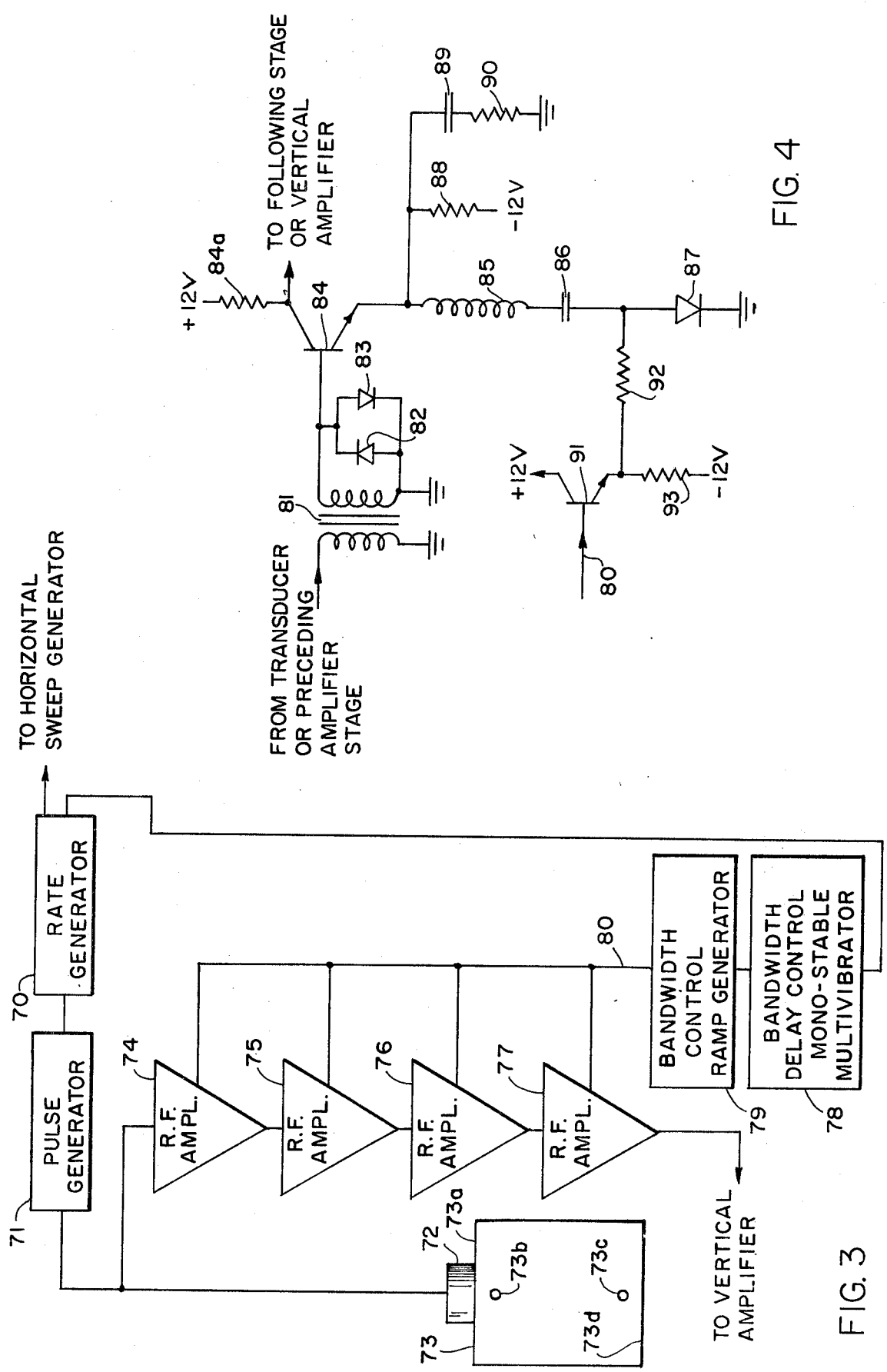

TIME-VARIABLE BANDWIDTH ULTRASONIC TESTING APPARATUS

BACKGROUND

In pulse-echo nondestructive testing employing ultrasonic wavetrains, resolution of defects and penetration of material are known to be inherently conflicting requirements. Yet, typical test aplications do involve simultaneous detection of defects close to the sound-beam entry surface as well as deep within the test object.

Near-surface resolution is usually achieved by the use of short wavetrains having only one or two cycles of the nominal test frequency and a correspondingly high harmonic content. Amplification of these without distortion and undesirable pulse stretching requires wideband amplifiers which tend to produce high background noise, particularly at the very high gains needed to detect small defects through the full cross section of typical test samples. Conversely, deep penetration of material is best obtained using relatively long wavetrains having several cycles of carrier and negligible higher order harmonic content. These wavetrains are compatible with tuned amplifiers of limited bandwidth which can have very high gain without excessive noise. As a result of these conflicting requirements, typical prior art instrumentation for ultrasonic flaw detection has involved compromises in amplifier design which limit optimum performance as discussed in the text by Krautkramer, ULTRASONIC TESTING OF MATERIALS, Springer-Verlag, N.Y., 1969, pg, 165-166.

Various solutions have been proposed heretofore for optimizing test results, exemplified as follows. Weighart in U.S. Pat. No. 3,033,029 describes a distance-amplitude compensation system based on time-varied receiver gain. Weighart in U.S. Pat. No. 3,309,914 proposes the use of a multi-frequency testing system to achieve both resolution and penetration. Couture in U.S. Pat. No. 3,823,603 employs a gated attenuator at the amplifier input to change system sensitivity abruptly. McElroy, et al, in U.S. Pat. No. 3,924,454 also use a multiple frequency test system with the addition of a search unit having a multi-element transducer.

In accordance with the present invention, performance is optimized by varying receiver-amplifier bandwidth as a function of time.

SUMMARY

Briefly described, ultrasonic nondestructive testing apparatus embodying the present invention is useful together with transducer means adapted to transmit ultrasonic energy into a test object in response to electrical signals and for deriving electrical signals in response to ultrasonic energy reflected from within the test object. The apparatus comprises means adapted to be coupled to the transducer means to supply electrical signals thereto and signal translating means having an input circuit adapted to be coupled to the transducer means for translating electrical signals derived by the transducer means in response to reflected ultrasonic energy and having an output circuit. The signal translating means exhibits a bandwidth that is varied over a range of bandwidths. Means coupled to the output circuit of the signal translating means are provided for utilizing electrical signals translated by the signal translating means.

DRAWINGS

FIG. 3 is a block diagram of apparatus in accordance with another embodiment of the present invention;

FIG. 4 is a detailed circuit diagram of a portion of the apparatus represented in FIG. 3.

DESCRIPTION

Figure 1:
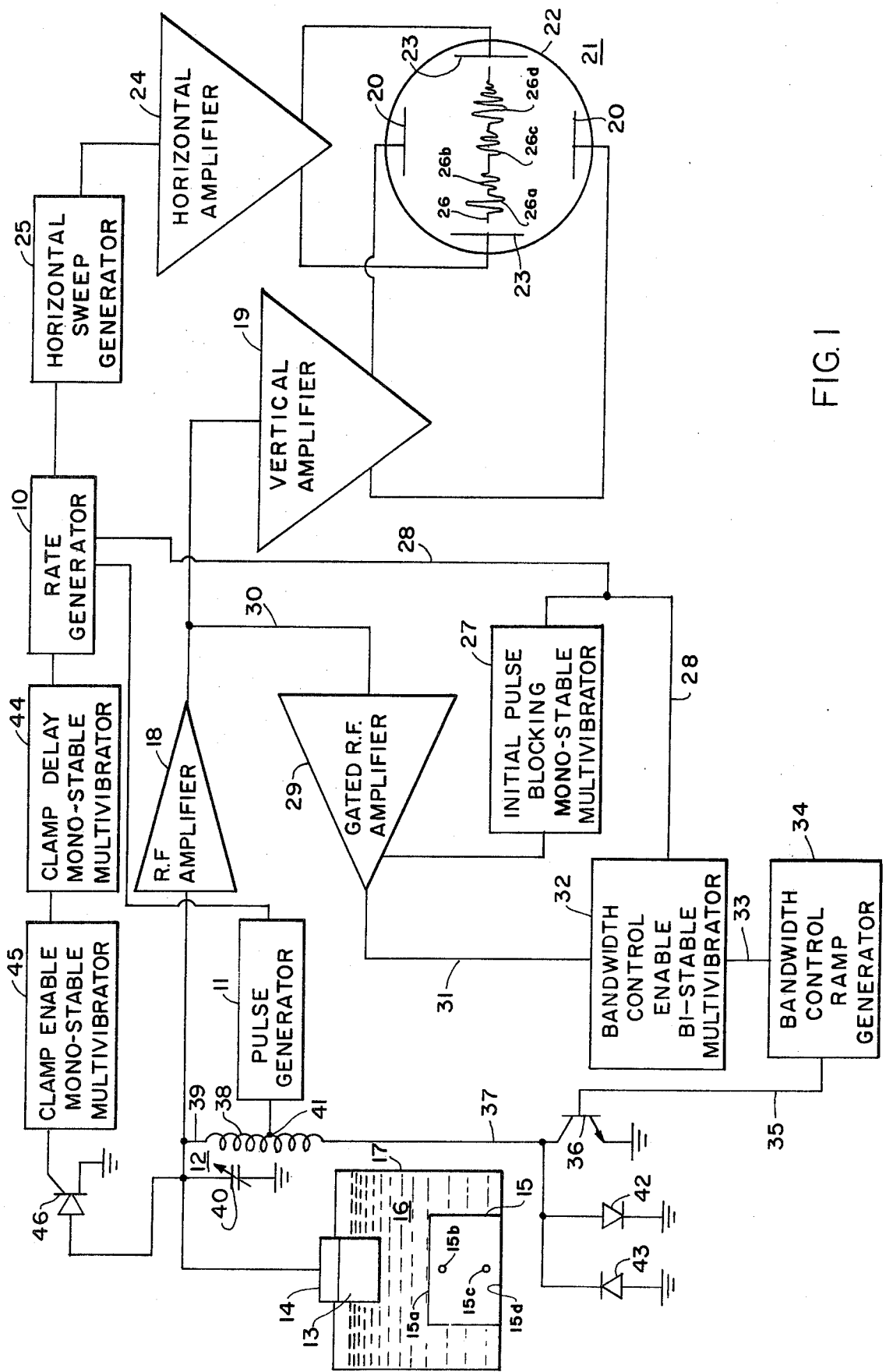
FIG. 1 is a schematic diagram, partly in block form, of ultrasonic nondestructive testing apparatus embodying the present invention.

Referring now to FIG. 1 of the drawings, the present invention is particularly adapted to be embodied in ultrasonic nondestructive testing apparatus which may take any of a variety of forms. In this instance it includes a rate generator or clock 10 adapted to produce repetitive electrical pulses which time the operation of a pulse generator 11 coupled via a tuned or resonant circuit 12 to be described more fully hereinafter, to a search unit which includes a piezo electric element or transducer 13 of conventional construction. Element 13 is adapted to convert electrical pulses from pulse generator 11 into pulses of ultrasonic energy and to derive electrical signals in response to reflected ultrasonic energy and may be provided with an energy-absorptive backing or damping member 14 of known construction. Transducer 13, 14 is shown acoustically coupled to a test object 15 by the immersion of both in a liquid or couplant 16 within a container 17.

Resonant circuit 12 is included in the input circuit of a radio frequency amplifier 18 of one or more stages of amplification having its output circuit coupled to a vertical amplifier 19, in turn, coupled to the vertical deflection plates 20 of a conventional cathode ray tube or display device 21. Display device 21 has a viewing screen 22 and horizontal deflection plates 23 coupled to the output of a horizontal amplifier 24. A horizontal sweep generator 25 coupled to and synchronized by rate generator 10 supplies a saw tooth sweep signal to horizontal amplifier 24. Thus, a horizontal trace 26 is developed on viewing screen 22 during repetitive time intervals exhibiting vertical excursions 26a, 26b, 26c and 26d, representing reflecting surfaces or discontinuities such as the front surface 15a, defects 15b and 15c and rear surface 15d of test object 15 in a manner well understood in the art. The portion of the apparatus thus far described may be of conventional construction.

The apparatus further includes an initial-pulse-blocking monostable multivibrator 27 having its control circuit connected by a lead 28 to rate generator 10. The output of multivibrator 27 is supplied to the control circuit of a gated radio frequency amplifier 29 whose input circuit is connected by a lead 30 to the output of radio frequency amplifier 18 and whose output circuit is connected to by a lead 31 to one control circuit of a bandwidth-control bistable multivibrator 32, the remaining control circuit of which is connected by an extension of lead 28 to rate generator 10. The output circuit of multivibrator 32 is connected by a lead 33 to the control circuit of a bandwidth-control ramp generator 34. Units 27, 29, 32 and 34, individually, may be of conventional construction and function in a manner well understood in the art.

The output of generator 34 is connected by a lead 35 to the base of an NPN transistor 36 which functions as a variable resistance responsive to control signals supplied over lead 35. The emitter of transistor 36 is grounded and its collector is connected by a lead 37 to one terminal of an inductor 38 included in tuned circuit 12. The remaining terminal of inductor 38 is connected by a lead 39 to the connection between transducer 13, 14 and RF amplifier 18. Tuned circuit 12 also includes an adjustable or tuning capacitor 40 having one set of its plates connected to an extension of lead 39 and its remaining set grounded. Tuned circuit 12 is resonant at a given frequency and in this application it may be in a range from 0.5 Megahertz (MHz) to 20 MHz. As is well understood in the art, bandwidth of a circuit is usually expressed as the difference between those frequencies at which the power output of the circuit is one-half that which occurs at the frequency of maximum power output. The bandwidth of resonant circuit 12 and the associated circuitry at the input of RF amplifier 18 is a function of inductance, capacitance and resistance and in this aplication is primarily dependent on the resistance of transistor 36. Assuming, in this example, an operating or resonant frequency of 5 MHz, the circuit parameters are selected so that in a response to a control signal of varying amplitude at lead 35, the bandwidth of the circuit varies from 5.0 MHz to 1.2 MHz during each of the repetitive testing intervals established by rate generator 10. In other words, at maximum bandwidth, the half-power points are at 2.5 MHz and 7.5 MHz while at minimum bandwidth, they are at 4.4 MHz and 5.6 MHz.

Pulse generator 11 is connected to a tap 41 on coil 38 positioned to provide appropriate impedance matching in a manner well understood and a pair of diodes 42, 43 connected in parallel in opposite polarity sense between lead 37 and ground effectively short circuit transistor 36 during each relatively high-amplitude pulse from pulse generator 11. Electrical signals from transducer 13, 14 produced in response to echoes are of insufficient amplitude to cause conduction in either of diodes 42 or 43.

In order to inhibit or terminate ringing in resonant circuit 12 after the application of each pulse from pulse generator 11, the apparatus includes a clamp delay monostable multivibrator 44 connected to and controlled by rate generator 10 having its output connected to and controlling a clamp enable monostable multivibrator 45, in turn, coupled via a silicon control rectifier 46 to tuned circuit 12. Multivibrators 44 and 45 may be of conventional construction.

Figure 2:
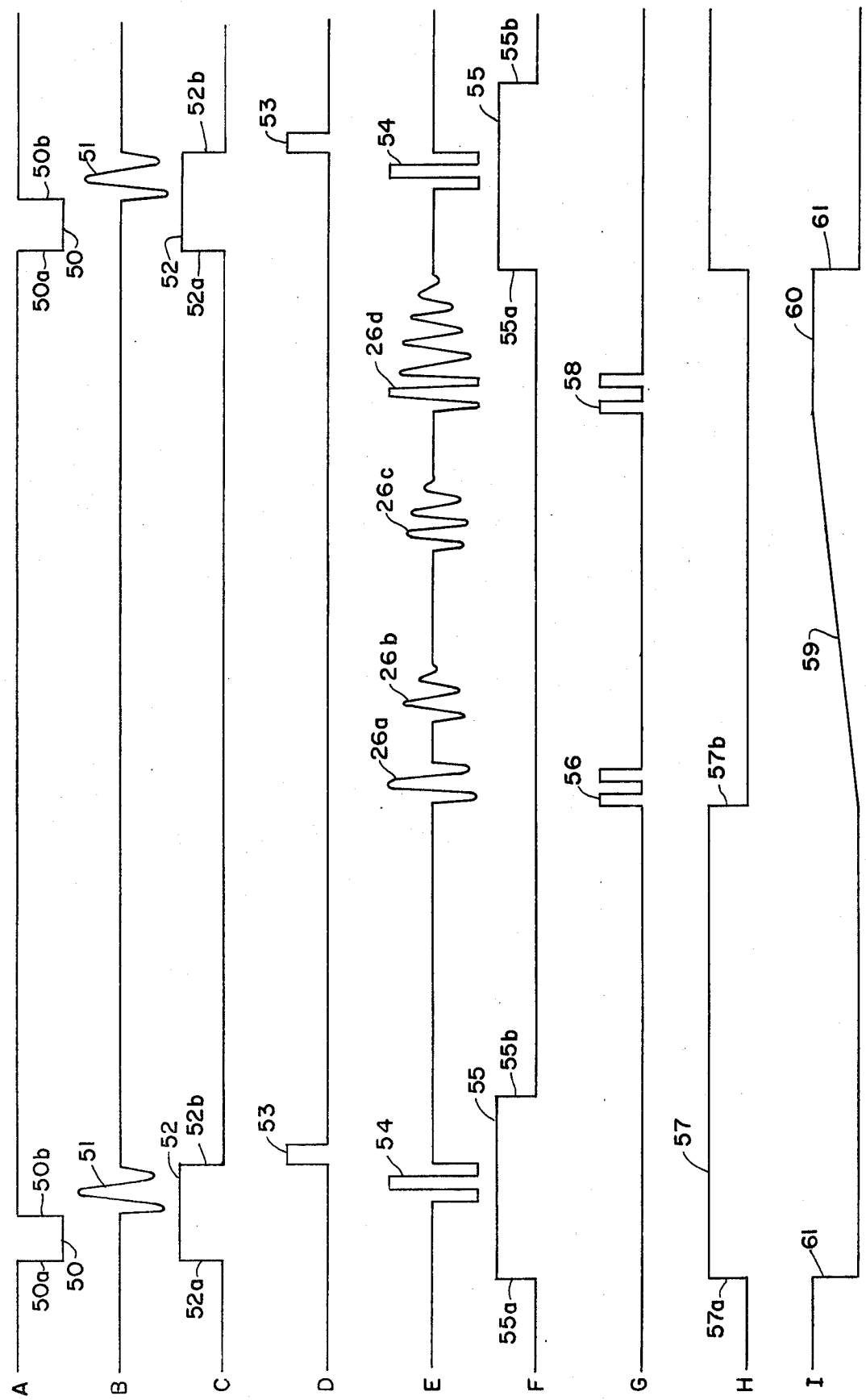
FIG. 2 shows a series of wave forms representing various signals which may be found in the apparatus illustrated in FIG. 1 plotted to the same time scale.

In describing the operation of the apparatus shown in FIG. 1, reference will be made to FIG. 2 of the drawings which represents wave forms of electrical signals that appear at various points in the apparatus plotted to the same time scale.

FIG. 2A illustrates the timing or clock pulses produced by rate generator 10 which control and synchronize various operations in the apparatus. Although only two such pulses 50 are shown, it is to be understood that these pulses are repetitive and continuous.

In response to trailing edge 50b of each pulse 50, pulse generator 11 produces an output pulse that is supplied to resonant circuit 12 and to transducer 13, 14. Resonant circuit 12 tends to continue oscillations or "ring" after the termination of each pulse from generator 11 and but for the operation of circuit elements 44, 45 and 46, the transmitted pulse would exhibit a long "tail." Diodes 42, 43 are conducting during this interval thereby shunting transistor 36. Instead, only limited excursions occur as represented by signal 51 in FIG. 2B. For this purpose, multivibrator 44 provides pulses 52 shown in FIG. 2C each of which is initiated (52a) with the leading edge 50a of a corresponding clock pulse 50 and which has a trailing edge 52b occurring a predetermined interval later. Multivibrator 45 is initiated with the occurence of trailing edge 52b to produce pulses 53 illustrated in FIG. 2D of relatively short duration which causes silicon control rectifier 46 to become conductive effectively short circuiting resonant circuit 12 thereby to inhibit or abruptly terminate ringing or free oscillations.

FIG. 2E contains a representation of the electrical signals supplied by radio frequency amplifier 18 to vertical amplifier 19 and, in turn, supplied to cathode ray display device 21 including signal portion 54 corresponding to the transmitted wave trains and portions 26a, 26b, 26c and 26d corresponding to front surface 15a, discontinuities or defects 15b and 15c and rear surface 15d of test object 15. As is well understood in the art, the timing of sweep generator 25 is adjusted so that signal portions 54 do not appear in the display on viewing screen 22 of display device 21.

As shown in FIG. 2F, multivibrator 27 produces pulses the leading edges 55a of each of which occur at the same time as leading edges 50a of clock pulses 50. The trailing edges 55b occur some time following pulse 51 (FIG. 2B) but prior to the expected occurrence of echo signals. Amplifier 29 is rendered inoperative during each pulse 55 and the first signal to occur thereafter having at least a selected amplitude, such as signal portion 56 shown in FIG. 2G (corresponding to front-face signal 26a shown in FIG. 2E), is supplied by amplifier 29 to multivibrator 32. Multivibrator 32 is also supplied with clock pulses from rate generator 10 so that it produces a square wave having undulations 57 (FIG. 2H) of one polarity whose leading edges 57a are coincident with leading edges 50a of clock pulses 50 and whose trailing edges 57b coincident with the initiation of signal 56 (FIG. 2G). Signal portion 58 corresponding to rear surface reflection signal 26d (FIG. 2E) which follows signal portion 56 occurs during a mode of operation of the multivibrator 32 wherein no activation or change of condition may be produced.

In response to trailing edge 57b of the square wave 57, bandwidth control ramp generator 34 is initiated to produce a control signal having a portion which varies substantially linearly with time as represented by ramp 59 in FIG. 2I followed by a portion 60 of essentially fixed amplitude which terminates at the occurrence of leading edge 50a of clock pulse 50. Control signal 59 causes the resistance of transistor 36 to vary during each repetitive testing interval. In other words, the ramping voltage 59 causes transistor 36 to turn on gradually thus connecting inductor 38 to ground through a decreasing impedance. Diodes 42, 43 are not conducting during this interval because applied electrical signals are below their conductivity thresholds. Thus, in accordance with the present invention, the bandwidth of the signal translating circuit comprised of resonant circuit 12 and its associated circuitry including variable resistance or transistor 36 varies during each repetitive testing interval. Specifically, in this example, bandwidth changes linearly with time from an initial value of 5 MHz to a final value of 1.2 MHz during each ramp 59. The signal translating circuit exhibits a wide bandwidth for the early-occurring "close in" echoes and a progressively narrower bandwidth with time. Therefore, the ability of the apparatus to define near-surface defects or discontinuities is excellent while the progressively narrowing bandwidth affords improved ability to detect defects or discontinuities deep within a test object. This is of particular importance in the inspection of test objects composed of acoustically noisy or highly attenuative materials.

In the embodiment of the invention shown in FIG. 3 of the drawings, the bandwidth of each of a plurality signal translating stages connected in cascade is varied during repetitive testing intervals.

A rate generator 70 is coupled to and controls a pulse generator 71, in turn, coupled to a transducer or search unit 72 which may include a piezo electric element and be of conventional construction shown in direct contact with a test object 73. Under the control of generator 70, pulse generator 71 supplies electrical pulses to transducer 72 which projects pulses of ultrasonic energy into test object 73.

Transducer 72 is also coupled to a radio frequency amplifier 74 constructed in a manner to be described hereinafter, in turn, coupled to similar amplifiers 75, 76 and 77 in cascade. The output of amplifier 77 is coupled to a vertical amplifier, such as amplifier 19 shown in FIG. 1 which is coupled to a display device as there illustrated. In order to control the bandwidth of amplifiers 74–77, rate generator 70 is coupled to a bandwidth delay control monostable multivibrator 78 whose output is supplied to a bandwidth-control ramp generator 79. The output of generator 79 is supplied over lead 80 and extensions thereof to control circuits of each of the amplifiers 74–77.

Each of the amplifiers 74–77 may be constructed in the manner shown in FIG. 4 of the drawings. Signal input from the transducer 72 or from a preceding amplifier stage is supplied to the primary winding of a coupling transformer 81 the secondary of which is connected in parallel with diodes 82 and 83 connected in opposite polarity sense and which perform an amplitude limiting function with respect to pulses from generator 71. The secondary winding of transformer 81 is also connected to the base of an NPN transistor 84 connected to function as an amplifier in a well-known manner and having a positive supply voltage source connected via a load resistor 84a to its collector. The collector of transistor 84 is coupled to a following stage or to the vertical amplifier associated with a display device and its emitter is connected to one terminal of an inductor 85 having its other terminal connected to a condenser 86 that is connected to ground through a diode 87. A source of negative supply voltage is connected through a resistor 88 to the emitter of transistor 84 and the emitter is connected to ground through series-connected condenser 89 and resistor 90 which determine the gain of transistor-amplifier 84 in its broad-band condition. The control voltage at lead 80 is supplied via an emitter-follower 91 and a resistor 92 to diode 87 and a resistor 93 is connected between a source of negative supply voltage and the junction of the emitter of transistor 91 and resistor 92.

Amplifier 84 has a fixed load resistor 84a in its collector circuit and a variable emitter load. As is well known, the gain of amplifier 84 is dependent on the collector load divided by the emitter impedance. With the control signal at lead 80 at its minimum, diode 87 is non-conductive and the series circuit consisting of inductor 85 and condenser 86 does not influence the bandwidth of the circuit, i.e., the bandwidth is at its greatest since gain and bandwidth are determined by emitter load 88, the capacitance of condenser 89, the resistance of resistor 90 and the current through diode 87. As the voltage at lead 80 increases with time, current flow through diode 87 increases and the diode presents a progressively decreasing impedance in the circuit. The series circuit consisting of inductor 85, condenser 86 and diode 87 thus cause the amplifier to exhibit a progressively narrower bandwidth during each of the repetitive testing intervals.

Figure 5:
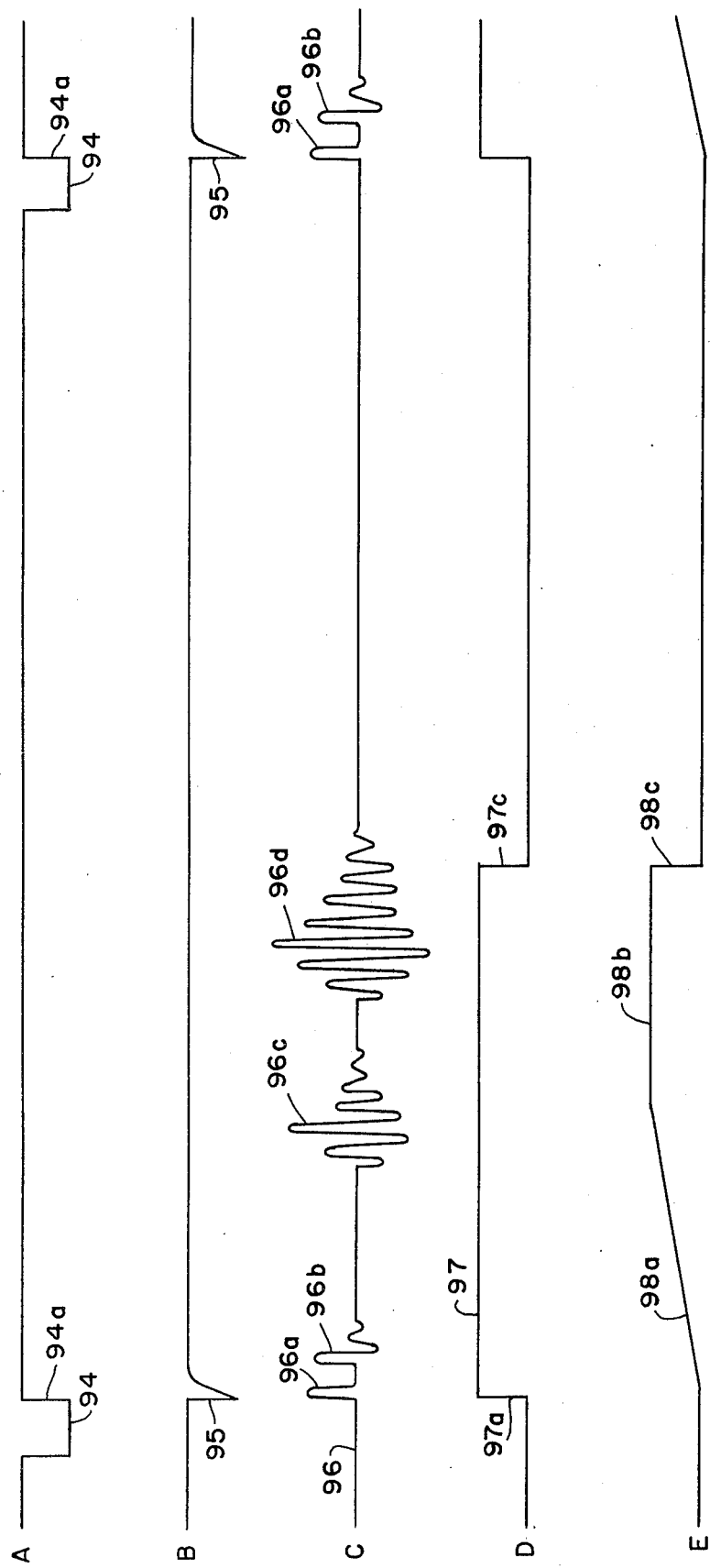
FIG. 5 shows a series of waveforms representing various signals which may be found in the apparatus shown in FIG. 3 plotted to the same time scale.

In the operation of the embodiment of the invention shown in FIGS. 3 and 4, rate generator 70 produces repetitive clock pulses 94 represented in FIG. 5A of the drawings which control pulse generator 71 so that each output pulse from generator 71 is initiated at the trailing edge 94a of each clock pulse. Except for the differences in timing required by virtue of the absence of a water path to front face 73a of test object 73, the apparatus functions in a manner similar to the apparatus shown and described in connection with FIG. 1.

As represented in FIG. 5C, the signal 96 at the output of amplifier 77 includes pulses 96a that correspond in timing with pulses 95 from pulse generator 71. Echoes 86b and 96c represent defects or discontinuities 73b and 73c in test object 73 and echo 96d represents the rear surface 73d of the test object.

Multivibrator 78 is initiated at the time of each of the trailing edges 94a of clock pulses 94 and the leading edge 97a (FIG. 5D) of each of its output pulses 97 initiates the ramp portion 98a (FIG. 5E) of the control signal generated by generator 79. That signal has a portion 98b of essentially fixed amplitude and it returns (98c) to an initial state at the occurrence of the trailing edge 97c of pulse 97.

During each repetitive testing interval, each diode 87 in the several RF amplifiers 74–77 is varied in its resistance in response to ramp 98a thereby to vary the bandwidth of all of signal translating amplifiers 74–77 in unison in response to ramp 98a. The resonant frequency and bandwidth variation may be similar to that employed in connection with the embodiment of the invention shown in FIG. 1.

While two embodiments of the present invention have been disclosed, it will be readily apparent to those skilled in the art that numerous changes and modifications may be made thereto without departing from the spirit of the invention. For example, although the embodiment of FIG. 3 is shown in a contact testing application, with minor modification it may also be adapted to immersion testing as illustrated in FIG. 1. Also, in the FIG. 3 embodiment, conventional buffers may be used in advance of one or more of the several stages of RF amplification and an attenuator or attenuators may be included, as desired, Further, other circuit configuration may be utilized to achieve variable bandwidth in either the FIG. 1 or FIG. 3 embodiments of the invention. Accordingly, the scope of the present invention is defined only by the scope of the following claims.

We claim:

1. Ultrasonic nondestructive testing apparatus for use with transducer means adapted to transmit ultrasonic energy into a test object in response to electrical signals and for deriving electrical signals in response to ultrasonic energy reflected from an outer surface of and from within the test object, said apparatus comprising:

a pulser adapted to be coupled to the transducer means for supplying electrical signals thereto during repetitive testing intervals;

(a) signal translating means having an input circuit adapted to be coupled to the transducer means for translating electrical signals derived by the transducer means in response to reflected ultrasonic energy and having output circuit means, said input circuit including a resonant circuit exhibiting inductance and capacitance resonant at a selected frequency and having a variable resistance responsive to a control signal whereby said signal translating means exhibits a bandwidth variable over a range of bandwidths;

a control signal generator coupled to said variable resistance for deriving a control signal to vary said bandwidth of said signal translating means during each of said repetitive testing intervals;

means operable synchronously with said pulser and coupled to said resonant circuit for inhibiting free electrical oscillations in said resonant circuit at a selected time following a pulse of said electrical signals derived by said pulser;

means coupled to said output circuit means and responsive to signals translated by said signal translating means for initiating said control signal in response to a signal representing ultrasonic energy reflected from an outer surface of the test object; and means coupled to said output circuit means of said signal translating means for utilizing electrical signals translated by said signal translating means.

2. Ultrasonic nondestructive testing apparatus in accordance with claim 1 wherein said means for inhibiting free oscillations includes a control device coupled to said resonant circuit and adapted to exhibit a low resistance selectively in synchronism with electrical signals derived by said pulser.

3. Ultrasonic nondestructive testing apparatus in accordance with claim 1 further comprising means operable in synchronism with electrical signals derived by said pulser for reducing substantially the resistance of said variable resistance essentially in time-coincidence with each pulse of said electrical signals.

4. Ultrasonic nondestructive testing apparatus for use with transducer means adapted to transmit ultrasonic energy into a test object in response to electrical signals and for deriving electrical signals in response to ultrasonic energy reflected from an outer surface and from within the test object, said apparatus comprising:

a pulser adapted to be coupled to the transducer means for supplying electrical signals thereto during a relatively short period of time during each of repetitive testing intervals;

signal translating means including an input circuit adapted to be coupled to the transducer means for translating electrical signals derived by the transducer means in response to reflected ultrasonic energy and including first and second output circuit means, said input circuit including a resonant circuit exhibiting inductance and capacitance resonant at a selected frequency and having a variable resistance responsive to a control signal whereby said signal translating means exhibits a bandwidth variable over a range of bandwidths, and said signal translating means being adapted to translate electrical signals continously to said first output circuit means and including a gate circuit for establishing active and quiescent states whereby said signal translating means translates electrical signals to said second output circuit means substantially only during each of said active states;

means coupled to said gate circuit of said signal translating means for deriving gating signals in synchronism with the electrical signals derived by said pulser, each such gating signal including a quiescent-state-producing portion having a leading edge essentially time-coincident with the initiation of one of said short periods of the electrical signals supplied by said pulser and having a trailing edge following the end of said short period but occurring prior to the arrival of ultrasonic energy reflected from an outer surface of the test object;

a control signal generator having an output circuit coupled to said variable resistance and having an activating circuit coupled to said second output circuit means of said signal translating means for deriving a control signal to vary said bandwidth of said signal translating means during a portion of each of said repetitive testing intervals, said control signal being initiated essentially in time-coincidence with the occurrence of ultrasonic energy reflected from an outer surface of the test object;

means operable synchronously with said pulser and coupled to said resonant circuit for inhibiting free electrical oscillations in said resonant circuit at a selected time following the end of each of said short periods of the electrical signals supplied by said pulser; and means coupled to said first output circuit means of said signal translating mean for utilizing electrical signals translated by said signal translating means.

* * * * *